June 5, 1951 N. GRILLO Plant Pat. 1,013
HYBRID TEA ROSE PLANT
Filed Jan 6, 1950
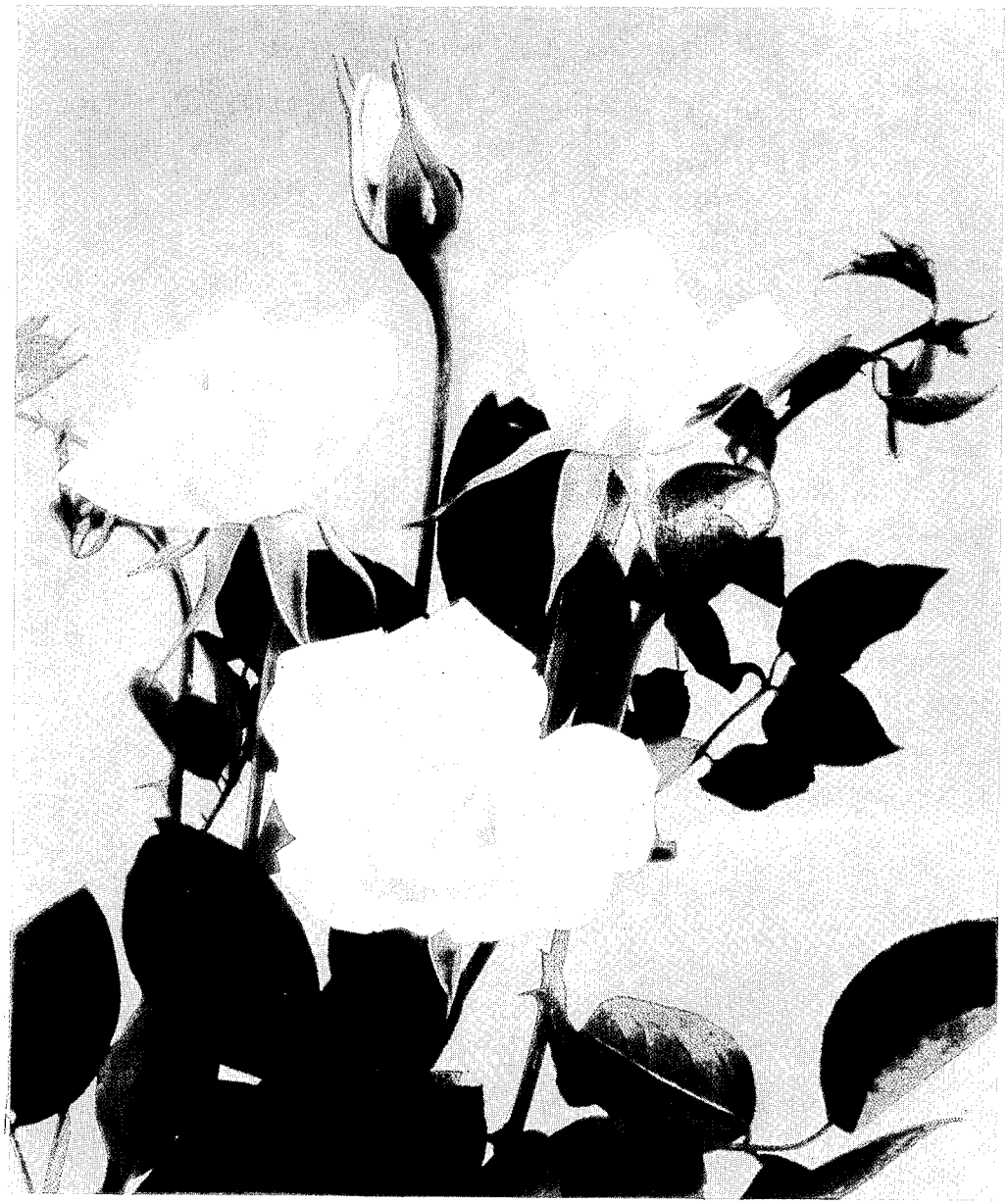
INVENTOR
Nicholas Grillo
By Orville M. Kile
Plant Pat. Agt.

Patented June 5, 1951

Plant Pat. 1,013

UNITED STATES PATENT OFFICE 1,013

HYBRID TEA ROSE PLANT

Nicholas Grillo, Milldale, Conn.

Application January 6, 1950, Serial No. 137,109

1 Claim. (Cl. 47—61)

My present discovery is primarily of the greenhouse type of hybrid tea rose plant, but also is adaptable to garden culture. The variety originated in my greenhouses at Milldale, Connecticut, as a sport of the variety Joanna Hill (unpatented) and resembles its parent in some respects, the principal differences being in its habits of growth and blooming and in the color of its flower. Reproduction by me at the same location, by means of budding, has shown the characteristics of this variety to be permanent.

The accompanying illustrations shown in approximately true colors, four specimens of the bud and flower of this new variety in various stages of opening, together with portions of the stem and foliage.

In the following detailed description, color plate numbers refer to Ridgway's Color Standards and Nomenclature. Where other colors are mentioned, the ordinary dictionary meaning of the term is intended.

*The plant*

Growth: Upright bush, with many very strong and exceptionally long stems.

Blooming habit: Breaks very fast and is one of the most free-blooming varieties known to me.

Stems: Straight and very strong and exceptionally long. Has very few thorns.

Foliage: Three to five leaflets.

*Size.*—Large.

*Quantity.*—Abundant, and situated close to flower.

*Shape.*—Long oval, with rounded base and acuminate apex.

*Color.*—Slightly darker than Forest Green (Plate XVII) but in the same color range. The under surface is Light Bice Green (Plate XVII) or slightly more gray.

*Rachis.*—Short; grooved above; slender.

*Veins.*—Prominent. Leaflet deeply grooved at midrib.

*Stipules.*—Long and narrow; clinging.

*The flower*

Bud:

*Shape.*—Very long and of "perfect" formation.

*Size.*—Medium.

*Opening.*—Opens gradually and fully.

*Color.*—Approximately Coral Pink (Plate XIII), petals sometimes edged with slightly darker shade (Old Rose, Plate XIII). Base of petal is greenish-yellow, approximately Pinard Yellow (Plate IV).

Bloom:

*Size.*—Large, averaging about 4½ inches in diameter.

*Borne.*—Singly on long stems.

*Form.*—High-centered, opening in loose formation but with center usually remaining mostly covered. Petals quill early.

*Petalage.*—From 25 to 35 petals.

*Color.*—This is distinctly a bi-color rose. Under surface of petal is Eosine Pink (Plate I) to Grenadine (Plate II). The inner surface is Pale Salmon Color (Plate XIV) to Shrimp Pink (Plate I). Turns darker with age, particularly on the outer surface, which is then approximately Alizarine Pink (Plate XIII).

*Fragance.*—Moderate.

*Behavior.*—Clings and dries.

*Longevity.*—Very good.

Petals:

*Size.*—Outer petals are approximately 2 inches long by 1½ inches wide. Inner petals are very much smaller and a number of the central ones are almost petaloids.

*Shape and arrangement.*—Obovate. All but the central petals reflex very early and roll backward at sides, thus forming very pointed or "quilled" petals. Most of the central petals and petaloids remain loosely curled over center of flower, showing the color of their under surface.

*Texture.*—Substantial.

*Appearance.*—Outer petals appear rather leathery but the smaller, inner petals appear silky.

Reproductive organs:

*Pistils.*—Tightly bunched in center of flower. *Styles*—short and rather even. Red. *Stigmas*—light yellow, approximately Pinard Yellow (Pl. IV).

*Stamens.*—Many, surrounding pistils. *Filaments*—light yellow, approximately Pinard Yellow (Pl. IV). Some rather long, making the area covered by stamens large—an inch or more in diameter in most specimens. *Anthers* — large. Brilliant yellow, approximately Light Cadmium (Pl. IV).

*Ovaries.*—Partly enclosed in calyx.

*Comparison*

The variety most like my new variety is its parent, Joanna Hill, from which it differs chiefly in the following respects:

1. The growth of my new variety is stronger, producing stronger canes.

2. My variety produces no blind wood as Joanna Hill does.

3. My variety produces straighter and longer stems.

4. My variety is a much more prolific producer of good blooms.

5. The foliage of my variety is more abundant and is situated closer to the flower.

6. The foliage of my variety is a little darker in color.

7. The color of the flower of my variety is different and is distinctly bi-color.

Having thus disclosed my discovery, I claim:

The new and distinct variety of hybrid tea rose plant, substantially as herein shown and described, characterized particularly by its very strong growth without production of blind wood; its exceedingly prolific production of flowers; its long, straight, strong stems; its abundant dark green foliage which comes up close to the flowers; and its bi-color flower of varying pink and apricot shades and with "quilled" form.

NICHOLAS GRILLO.

REFERENCES CITED

The following references are of record in the file of this patent:

UNITED STATES PATENTS

| Number | Name | Date |
|---|---|---|
| Pl. Pt. 137 | Nicolas | Aug. 30, 1935 |
| Pl. Pt. 201 | Aicardi | Oct. 13, 1936 |
| Pl. Pt. 521 | Lammerts | May 26, 1942 |
| Pl. Pt. 921 | Swim | Feb. 7, 1950 |